(12) United States Patent
Seiwert et al.

(10) Patent No.: US 9,919,081 B2
(45) Date of Patent: Mar. 20, 2018

(54) LIQUIDS AND GELS FOR THE OPHTHALMOLOGY AND MICROSCOPY SYSTEM FOR OBSERVING THE SAME

(71) Applicant: Carl Zeiss Meditec AG, Jena (DE)

(72) Inventors: Anja Seiwert, Aalen (DE); Christoph Hauger, Aalen (DE); Roland Guckler, Aalen-Dewangen (DE); Claude Moissonnier, Bonn (DE)

(73) Assignee: CARL ZEISS MEDITEC AG, Jena (DE)

( * ) Notice: Subject to any disclaimer, the term of this patent is extended or adjusted under 35 U.S.C. 154(b) by 469 days.

(21) Appl. No.: 14/524,341

(22) Filed: Oct. 27, 2014

(65) Prior Publication Data

US 2015/0119835 A1 Apr. 30, 2015

(30) Foreign Application Priority Data

Oct. 29, 2013 (DE) .................. 10 2013 017 948

(51) Int. Cl.
*A61M 31/00* (2006.01)
*A61M 1/00* (2006.01)
*A61B 3/10* (2006.01)
*A61B 3/13* (2006.01)
*A61F 9/007* (2006.01)
(Continued)

(52) U.S. Cl.
CPC ........... *A61M 1/0031* (2013.01); *A61B 3/102* (2013.01); *A61B 3/13* (2013.01); *A61F 9/00745* (2013.01); *A61K 49/0423* (2013.01); *A61M 1/0064* (2013.01); *A61F 2009/00887* (2013.01)

(58) Field of Classification Search
CPC ... A61B 3/102; A61M 1/0031; A61M 1/0064; A61K 49/0423; A61F 9/00745
USPC ................................ 604/66, 65, 48
See application file for complete search history.

(56) References Cited

U.S. PATENT DOCUMENTS 5,204,331 A * 4/1993 Nishi ................... A61K 9/0048
514/54
8,066,769 B2 * 11/2011 Werblin ................ A61F 2/1648
623/6.32
(Continued)

FOREIGN PATENT DOCUMENTS

DE 198 53 007 A1 5/2000
DE 10 2009 037 708 A1 3/2011
(Continued)

OTHER PUBLICATIONS

German Office Action issued in corresponding German patent application DE 10 2013 017 948.3, dated Aug. 1, 2014.
(Continued)

*Primary Examiner* — Edelmira Bosques
(74) *Attorney, Agent, or Firm* — Patent Portfolio Builders PLLC (57) ABSTRACT

Embodiments relate to an ophthalmology microscopy-system and a method of operating an ophthalmology microscopy-system which allow for an at least partial or full removal of liquids and gels used in ophthalmology for application in an eye of a patient in an particularly efficient way. Further embodiments relate to a product such as a liquid or a gel usable for an application in an eye of a patient, wherein the product has a high transmittance and, nevertheless, may be made visible particularly well.

12 Claims, 3 Drawing Sheets

(51) Int. Cl.
  *A61K 49/04* (2006.01)
  *A61F 9/008* (2006.01)

(56) References Cited

U.S. PATENT DOCUMENTS

| | | | |
|---|---|---|---|
| 2007/0066978 A1* | 3/2007 | Schafer | A61B 5/02007 606/128 |
| 2011/0112472 A1* | 5/2011 | Jacobson | A61F 9/00736 604/67 |
| 2011/0199577 A1 | 8/2011 | Wilzbach et al. | |
| 2012/0300294 A1 | 11/2012 | Jess et al. | |
| 2013/0226072 A1 | 8/2013 | Kraus et al. | |
| 2014/0362343 A1 | 12/2014 | Hauger et al. | |
| 2015/0002814 A1 | 1/2015 | Seesselberg et al. | |

FOREIGN PATENT DOCUMENTS

| | | |
|---|---|---|
| DE | 10 2010 033 825 A1 | 2/2012 |
| DE | 10 2010 047 011 A1 | 4/2012 |
| DE | 10 2013 009 817 A1 | 12/2014 |
| DE | 10 2013 010 844 A1 | 12/2014 |
| WO | 2012/159752 A2 | 11/2012 |

OTHER PUBLICATIONS

Auffarth, Gerd U., "Ophthalmic Viscoelastic Devices (OVD) in Ocular Surgery," 1st Edition—Bremen; UNI-MED Science, 2012, ISBN 978-3-8374-1281-9 and ISBN 978-1-84815-172-7.

Hirata, F. et al., "Visualization of residual perfluorocarbon liquid using intravitreal triamcinolone acetonide," Ophthalmic Surg. Lasers Imaging., Mar.-Apr. 2005; 36(2), pp. 169-172, http://www.ncbi.nlm.nih.gov/pubmed/1579233.

Leitgeb, R. et al., "Performance of fourier domain vs. time domain optical coherence tomography," Optics Express, vol. II, No. 8, pp. 889-894, Apr. 21, 2003.

* cited by examiner

LIQUIDS AND GELS FOR THE OPHTHALMOLOGY AND MICROSCOPY SYSTEM FOR OBSERVING THE SAME

CROSS-REFERENCE TO RELATED APPLICATION

The present application claims priority of Patent Application No. 10 2013 017 948.3, filed Oct. 29, 2013 in Germany, the entire contents of which are incorporated by reference herein.

FIELD

The present disclosure relates to an ophthalmology system which is particularly well suited for observing liquids and gels in an eye. Furthermore, the present disclosure relates to liquids and gels for application in an eye of a patient. The eye may be a mammal eye or human eye, for example.

BACKGROUND

Such ophthalmology systems include ophthalmology microscopes (also known as ophthalmic surgical microscopes) and optical coherence tomography (OCT) systems.

Ophthalmology microscopes are optical reflected light microscopes used during medical surgery in the ophthalmology and provide an image magnification of usually 5 to 30 times. In comparison to other optical reflected light microscopes, ophthalmology microscope have an increased focal length of the objective system in use of typically 175 mm to 550 mm. In this respect, ophthalmology microscopes are characterized in that they often do not directly image a fundus (fundus oculi/eyeground) of an eye but indirectly image the fundus of the eye. This is performed by imaging an intermediate image of the fundus of the eye wherein the intermediate image is generated by a lens of the eye together with an ophthalmology loupe (magnifying glass) disposed in front of the eye. The ophthalmology loupe is disposed at a distance of 4 mm to 80 mm from the lens of the eye. The ophthalmology loupe may be mounted to the ophthalmology microscope in a pivotable and/or releasable and/or exchangeable way. The field of view of ophthalmology microscopes, i.e. the area in the focal plane on the fundus which can be imaged onto the retina of a user by at least one imaging beam path at a particular point in time is typically greater than 1 mm$^2$. Therefore, the field of view of an ophthalmology microscope does not only comprise one single image point, as in the case of scanning microscopes; instead, at each point in time, a multi-dimensional (two- or three-dimensional) imaging of the inspected object is performed by the ophthalmology microscope (into an image plane).

In order to provide a spatial impression of the object to be imaged to a user, which is especially necessary for surgeries of the eye, ophthalmology microscopes are often stereo microscopes simultaneously providing at least one pair of imaging beam paths to the eyes of the user, wherein optical axes of the imaging beam paths of the at least one pair intersect in proximity of a focal plane of the ophthalmology microscope at a stereo angle of 0.5° to 14°.

The image of the object imaged by the ophthalmology microscope is may be provided by an ocular (for stereoscopic ophthalmology microscopes by a pair of oculars) to a user. Additionally or alternatively, the image may be converted to electric signals by an image converter (for stereoscopic ophthalmology microscopes by a stereo image converter or a pair of image converters, respectively) and visualized for the user by a monitor and/or a head-mounted display. This visualization using a monitor or head-mounted display may be performed in addition to usage of oculars or as an alternative to usage of oculars.

In order to meet the requirements of ophthalmology, ophthalmology microscopes often have an integrated slit lamp and/or keratoscope.

OCT-systems are devices in which light of a short coherence length is used for measuring distances of scattering materials using an interferometer in order to determine structural information within a volume of an object and, in turn, obtain a sectional view of an object to be analyzed by scanning point by point. This method is referred to as optical coherence tomography (OCT).

Today, OCT is already used frequently for inspections of the eye. In particular, OCT may be used during a cataract-surgery during which the natural lens is removed from the capsular bag after the lens has been shattered and an intraocular lens is inserted. However, it has been found that only structures having a sufficiently high reflectance are suitable for being observed using OCT.

Occasionally, it is necessary to visualize liquids and gels in the eye of a patient in the field of ophthalmology. These liquids and gels are, for example, used during surgery (in particular a cataract-surgery) and may, for example, serve as substitute materials for natural liquids (e.g. for stabilizing the eye chamber after drainage of a aqueous liquid) in order to protect, for example, the endothelium of the cornea from injury, in order to separate, for example, different tissue from each other, or in order to serve, for example, as a tampon. Examples of such liquids and gels are so-called OVDs (ophthalmic viscosurgical devices), balanced salt solutions, silicone oils or perfluorocarbons. These liquids and gels used in ophthalmology are often colorless in order to avoid hindering an observation of the eye by the surgeon during the surgery. Furthermore, these liquids and gels should be partially or entirely removed after a surgery as they may, for example, increase the intraocular pressure (particularly relevant for OVDs), affect the sight of the patient (particularly relevant for silicone oils), or act toxic (particularly relevant for perfluorocarbons).

Among the OVDs are, for example, chondroitin sulfate, sodium hyaluronate and hydroxypropylmethylcellulose. OVDs have in common that they are viscoelastic and, therefore, have a partially elastic and partially viscous material behavior.

Due to their high transmittance the removing and in particular the fully removing of the liquids and gels used in ophthalmology for application in the eye of a patient is very difficult.

During a cataract-surgery, a dull eye lens is destroyed during a phacoemulsification using supersonic sound or a laser, and the residual debris are removed from the eye by a suction apparatus. Then, an artificial lens is inserted. A suction apparatus configured to emit supersonic sound is used as a part of a phacoemulsification device. A viscoelastic gel is often used as a rinsing liquid.

It is an object of the present disclosure to provide an ophthalmology microscopy-system and a method of operating an ophthalmology microscopy system, wherein both provide at least partially or fully removing liquids and gels used in ophthalmology for application in the eye of a patient in a particularly efficient way.

It is an alternative object of the present disclosure to provide a product applicable for application in an eye of a patient, wherein the product is a liquid or a gel having a high transmittance and, nevertheless, is visualizable in a reliable way.

It is emphasized that not all embodiments must solve both objectives simultaneously. In fact, it is sufficient if an embodiment solves one or even none of the aforementioned objectives.

SUMMARY

Embodiments of an ophthalmology microscopy-system for application in a cataract-surgery comprise an imaging system, at least one photo detector, a suction apparatus, and a controller. The imaging system provides at least one imaging beam path imaging an object disposable in a focal plane of the imaging system in a magnifying way to a multi-dimensional (in particular two-dimensional) image of the object. The object may, for example, be the eye of a patient and, in particular, an eye chamber of the eye. The at least one photo detector is configured to detect an intensity of a radiation and to output an electric signal depending on the detected intensity of the radiation. The photo detector may, for example, be a CCD or CMOS-sensor. The detecting of the intensity of the radiation by the photo detector may be spatially resolving. The suction apparatus includes a suction pump which may be brought into a fluid connection to a suction head introducible into an eye of a patient. For example, the suction head may be introduced into the eye through an opening in the sclera. The controller (e.g. a microprocessor) is configured to control a suction rate of the suction pump of the suction apparatus depending on the electric signal output by the photo detector. The controlling of the suction rate of the suction pump may be automatically performed by the controller.

By controlling the suction rate of the suction pump by the controller in dependence of an intensity of radiation detected by the at least one photo detector, an automated adjusting of the suction rate to an amount of a substrate to be sucked off may be provided. This may provide a controlled and uniform sucking off of the substrate to be sucked off while simultaneously treating the eye with care.

According to an embodiment, the controller is configured to automatically detect the suction head of the suction apparatus in an image generated by the photo detector and to consider, for the controlling of the rate of the suction pump, a parameter of a spatial distance between the suction head and a source of at least a portion of the radiation detected by the photo detector.

The parameter of the spatial distance may be measured parallel to the object plane. In other words, the parameter of the spatial distance may represent a projection of the distance onto the object plane.

According to an embodiment, the photo detector is configured to detect an intensity of radiation emitted by a substitute material disposed in the eye of the patient, such as a viscoelastic substrate and/or silicone oil and/or perfluorocarbon. Such substitute materials may be introduced into the eye during the surgery. It may be advantageous to remove these substitute materials from the eye to a large fraction or to fully remove said substitute materials from the eye.

According to an embodiment, the substitute material is a viscoelastic substrate comprising at least 0.1 wt % chondroitin sulfate, in particular at least 0.5 wt % chondroitin sulfate, and/or at least 0.1 wt % sodium hyaluronate, in particular at least 0.5 wt % sodium hyaluronate, and/or at least 0.1 wt % hydroxypropylmethylcellulose, in particular at least 0.5 wt % hydroxypropylmethylcellulose, and/or at least 0.1 wt % of a sodium salt of hyaluronic acid, in particular at least 0.5 wt % of a sodium salt of hyaluronic acid.

According to an embodiment, the controller is configured to control the suction pump of the suction apparatus in a way that the suction rate of the suction pump increases when the intensity of the radiation emitted by the substitute material disposed in the eye of the patient and detected by the at least one photo detector increases. If a large amount of substitute material resides in the eye of the patient, operating the suction pump at a higher suction rate is possible.

According to an embodiment, the controller is configured to deactivate the suction pump of the suction apparatus as soon as the intensity of the radiation emitted by the substitute material disposed in the eye of the patient and detected by the at least one photo detector is less than a threshold-value. This threshold-value may be, for example, predetermined by a user. In addition or alternatively, the controller may be configured to activate the suction pump of the suction apparatus as soon as the intensity of the radiation emitted by the substitute material disposed in the eye of the patient and detected by the at least one photo detector is greater than or equal to the threshold-value.

According to an embodiment, a uniform threshold-value is used for the deactivating and the activating of the suction pump. According to an alternative embodiment, different threshold-values are used for the deactivating and the activating of the suction pump, wherein the threshold-value for the deactivating of the suction pump is below the threshold-value of the activating of the suction pump. According to an alternative embodiment, different threshold-values are used for the deactivating and the activating of the suction pump, wherein the threshold-value of the deactivating of the suction pump is below the threshold-value of the activating of the suction pump by at least 3%, and in particular at least 5%, of the absolute value of the threshold-value of the deactivating of the suction pump.

According to an embodiment, the controller is configured to ignore overshooting and undershooting of the threshold-value of less than 0.1 seconds, respectively. Therefore, it can be avoided that failure in the detecting of the intensity of the radiation by the photo detector or noise of the signal output by the photo detector causes activating and deactivating of the suction pump, respectively.

According to an embodiment, the substitute material comprises a fluorescent dye, in particular fluorescein. According to an embodiment, the substitute material comprises at least 0.01%, in particular 0.05%, of fluorescent dye.

According to an embodiment, the ophthalmology system includes an illumination system configured to emit radiation of an excitation band of the fluorescent dye towards an eye of a patient.

According to an embodiment, the photo detector is configured to determine an emission of the fluorescent dye relative to a fluorescence of a vitreous humor (Corpus vitreum) of the eye and to determine the intensity of the detected emission.

According to an embodiment, the ophthalmology microscopy-system includes an illumination system providing an illumination beam path and having at least one mode of operation in which radiation guided in the illumination beam path contains, in at least a section of the illumination beam path, an excitation band (spectral band of excitation radiation) of the fluorescent dye. In addition, the illumination beam path may, in at least this section of the illumination beam path, be essentially free of a fluorescent band (spectral band of fluorescent radiation) of the fluorescent dye.

In this context, "essentially free" means that the intensity of the radiation of the fluorescent band is less than the intensity of the radiation of the excitation by at least 80% and, in particular by at least 90% and more in particular by at least 98%.

According to an embodiment, the photo detector is then configured to suppress detecting radiation of the excitation band of the fluorescent dye relative to detecting radiation of the fluorescent band of the fluorescent dye. For example, a spectral sensitivity of the photo detector for all wavelengths of the excitation band may be less than 80% or less than 50% or less than 20% or less than 10% or less than 1% of the spectral sensitivity of the photo detector for at least one wavelength of the fluorescent band.

Furthermore, this may be achieved in that the photo detector is only sensitive to radiation of the fluorescent band and/or has a filter not being transparent for radiation of the excitation band but being essentially transparent for radiation of the fluorescent band.

According to an alternative embodiment, the imaging system then includes at least one optical observation filter suppressing a transmittance of the radiation of the excitation band of the fluorescent dye relative to a transmittance of the radiation of the fluorescent band of the fluorescent dye, wherein the least one optical observation filter is disposed in the at least one imaging beam path in front of the at least one photo detector in at least one mode of operation. The photo detector may be configured to detect both the radiation of the excitation band of the fluorescent dye and the radiation of the fluorescent band of the fluorescent dye.

According to an embodiment, the suction head, and in particular a hand piece of the suction head, includes an indicator, the status of which changes depending on the electric signal output by the at least one photo detector. Hence, a suction rate currently chosen by the suction apparatus may be indicated to a user. According to an embodiment, the indicator is a display. According to an alternative embodiment, the indicator is a status lamp According to an embodiment, the suction head is configured to suck off a liquid from the eye of the patient and/or rinse a rinsing liquid into the eye of the patient.

According to an embodiment, the suction apparatus includes a reservoir and the suction pump is connected to both the reservoir and the suction head via pressure-resistant conducts and is further configured to pump liquid from the eye of the patient into the reservoir via an opening in the suction head.

According to an embodiment, the ophthalmology microscopy-system includes a rinsing apparatus having a reservoir of liquid and a rinsing pump, wherein the rinsing pump is connected to both the reservoir of liquid and the suction head via pressure-resistant conducts. The rinsing pump is configured to pump liquid from the reservoir of liquid to the suction head and output the liquid into the eye of a patient via an opening in the suction head. The controller is then further configured to control the delivery rate of the rinsing pump of the rinsing apparatus in dependence of the electric signal output by the photo detector.

According to an embodiment, the suction head of the suction apparatus is configured to emit supersonic sound into the eye of a patient. In this respect, a supersonic sound source may be disposed inside the suction head, for example.

Embodiments of a method of operating an ophthalmology microscopy-system during a cataract-surgery comprises a detecting of radiation emitted by one of a viscoelastic substrate, a silicone oil and perfluorocarbon, wherein the viscoelastic substrate, the silicone oil and the perfluorocarbon are disposed in an eye of a patient; and an automatically adjusting of a suction rate of a suction pump of a suction apparatus connectable to a suction head introducible into the eye of the patient, wherein the automatic adjusting of the suction rate depends on an intensity of the detected radiation. For this, the ophthalmology microscopy-system may have the previously described configuration.

According to an embodiment, the method further comprises applying a substitute material comprising a fluorescent dye into the eye of the patient.

According to an embodiment, the method further comprises introducing the suction head into the eye of the patient before or after operating the suction pump.

Some embodiments comprise a computer programmed product comprising program steps configured to perform the previously described method when loaded in a microprocessor. The computer program product may, for example, be stored on a data memory or provided via the internet.

Embodiments provide a product for application in an optical coherence tomography method, wherein the product comprises a supporting agent suitable for being introduced into an eye. The supporting agent comprises a viscoelastic substrate or a silicone oil or a perfluorocarbon. Furthermore, the supporting agent comprises nano-particles being different from the supporting agent.

According to an embodiment, the nano-particles provide an increased extinction per centimeter of material thickness (supporting agent comprising nano-particles) in the visible light wavelength region of less than 6/cm, less than 5/cm, more in particular less than 4/cm, more in particular less than 3/cm, even more in particular less than 2/cm. This ensures that a visual perception of a surgeon is not hindered by the nano-particles. The extinction is defined as a negative logarithm to base 10 of a ratio of an intensity of light transmitted by the product to an intensity of light incident onto the product, wherein the light is in at least one of a visible light wavelength region and near-infrared light wavelength region. Outside of the visible light wavelength region, the extinction may be higher.

According to an embodiment, the nano-particles provide an increased extinction per centimeter of material thickness (supporting agent comprising nano-particles) in the visible light wavelength region of more than 1.25/cm, and in particular more than 1.5/cm.

The extinction represents a measure of an attenuation of an intensity of light transmitted through a region illuminated by light. The attenuation by the intensity of light transmitted through the region illuminated by the light may be caused by different physical processes. These physical processes comprise, for example, absorption, scattering and fluorescent excitation. In order to determine the extinction, light in the visible light wavelength region and/or near-infrared light wavelength region may be directed onto the product so that it traverses a distance of 1 cm, for example. The intensity of the transmitted light is determined essentially along the transmission direction in order to then determine a ratio of intensities of light transmitted through the product and of light incident onto the product.

The extinction is a property of the product depending on a structure and material along the transmission direction within the product. Furthermore, the extinction depends on a wavelength of the light in use. The extinction may be considered as an integrated value along a path along the transmission direction of the light transmitted through the product. The intensity $I_t$ of the transmitted light and the intensity $I_e$ of the incident light are related to each other by the Lambert-Beer law:

$$I_t = I_e \cdot \exp(-\tau \cdot D) \quad \text{Equation (1)}$$

Here, $\tau$ refers to the linear extinction coefficient of the product along the transmission direction and D refers to a length of the path along the transmission direction. The extinction is given by the following equation:

$$\text{extinction} = -\log_{10}\left(\frac{I_t}{I_e}\right) \quad \text{Equation (2)}$$

Therefore, the following equation relating the extinction and the linear extinction coefficient $\tau$ may be deduced:

$$\text{extinction} = \frac{1}{\ln 10} \cdot \tau \cdot D \quad \text{Equation (3)}$$

The extinction is determined using light in the visible light wavelength region and/or near-infrared light wavelength region by measuring the intensity $I_t$ of the transmitted light and the intensity $I_e$ of the incident light. Light in the visible wavelength region comprises electromagnetic waves having wavelengths in a region of roughly 400 nm to 700 nm. Light in the near-infrared wavelength region comprises electromagnetic waves having wavelengths longer than 700 nm up to roughly 2.5 µm, in particular up to roughly 1.3 µm. The extinction of the product being transmitted may be less than 6 per centimeter, in particular less than 5 per centimeter, in one or multiple regions of the visible light wavelength region and near-infrared light wavelength region. Therefore, the extinction does not need to be in between these limits for all regions in the visible light wavelength region and near-infrared light wavelength region.

If the mere supporting agent, i.e. the supporting agent in absence of nano-particles, is traversed by light in the visible light wavelength region and/or near-infrared light wavelength region along a length D, the extinction is less than $\log_{10} 2$. Therefore, at least half of the intensity of the incident light is transmitted through the supporting agent if the supporting agent does not comprise nano-particles (or a negligible amount of nano-particles) along the path of the transmitted light. Therefore, the mere supporting agent is essentially transparent for light in the visible light wavelength region and/or near-infrared light wavelength region.

The nano-particles may be distributed uniformly or non-uniformly in the volume of the supporting agent. The presence of the nano-particles in the supporting agent leads to an increased extinction compared to the case in which the nano-particles are absent, i.e. when mere the supporting agent is present. The increase of the extinction caused by the presence of the nano-particles may be calculated based on the configuration of the nano-particles and their properties as will be described below. The increased extinction may have a value of up to 5, in particular up to 6. Therefore, a ratio of intensities of the transmitted light and the incident light amounts to $10^{-6}$ in the at least one region of the product traversed by light at the threshold-value 6 of the extinction.

According to an embodiment, a reflectance of the product in the visible light wavelength region and/or near-infrared light wavelength region is increased due to the presence of the nano-particles by at least 0.1%, in particular at least 1%, more in particular at least 10%, more in particular at least 50%, and more in particular at least 100%. In this application, the reflectance refers to a fraction of an intensity of light reflected by the product essentially counter-directed to a direction of incidence of light incident onto the product. Therefore, the reflected light contributing to the determining of the reflectance essentially propagates in the direction opposite to the direction of incidence, wherein a direction of propagation of the reflected light may differ from the direction opposite to the direction of incidence by up to 10 degree, in particular up to 5 degree, and more in particular up 2 degree. The increase of the reflectance by, for example, at least 10% relative to the supporting agent without nano-particles is caused by the presence of the nano-particles. The increase the reflectance advantageously provides an increased signal if the product is imaged using an OCT-system. Thus, by having a product comprising nano-particles, the product can be made visible when imaged by an OCT.

According to an embodiment, the supporting agent is a viscoelastic substrate different from the vitreous humor of an eye, wherein the viscoelastic substrate comprises at least 0.1 wt % chondroitin sulfate, in particular at least 0.5 wt % chondroitin sulfate, and/or at least 0.1 wt % sodium hyaluronate, in particular at least 0.5 wt % sodium hyaluronate and/or at least 0.1 wt % hydroxypropylmethylcellulose, in particular at least 0.5 wt % hydroxypropylmethylcellulose, and/or at least 0.1 wt % of a sodium salt of hyaluronic acid, in particular at least 0.5 wt % of a sodium salt of hyaluronic acid. Such a supporting agent has an extinction and reflectance roughly corresponding to that of the vitreous humor. However, such a supporting agent is perceptible/visible where the nano-particles are present.

According to an embodiment, the product has a pH between 6.8 and 7.6, in particular between 7.0 and 7.4.

According to an embodiment, at least 80 wt %, in particular at least 90 wt %, of the nano-particles have an extension between 1 nm and 100 nm, in particular between 2 nm and 50 nm, more in particular between 10 nm and 20 nm. The nano-particles may have different forms such as essentially spherical, elliptical or the like, and, therefore, may have different diameters along different direction. The extension of a nano-particle may be considered as a largest diameter of this nano-particle. A minimum diameter of the nano-particle may be between 1 nm and 100 nm, in particular between 2 nm and 50 nm, more in particular between 10 nm and 20 nm. Nano-particles of this extension are commercially available.

According to an embodiment, at least 80 wt %, in particular at least 90 wt %, of the nano-particles comprise a metal, in particular gold, silver, titanium, copper, cobalt, nickel and/or iron. In addition or alternatively, at least 80 wt %, in particular 90 wt %, of the nano-particles may comprise silicone and/or oxygen. Furthermore, at least 80 wt %, in particular at least 90 wt %, of the nano-particles may consist of at least 10 wt % of one of a metal, silicon, or oxygen or may consist of at least 10 wt % of a combination of a metal and/or silicon and/or oxygen. In this respect, in particular the metal may be disposed as a shell on a core comprising silicone. An advantage of nano-particles having an inert metal such as gold on their surface is, for example, biological compatibility.

According to an embodiment, a previously described product is used in an OCT method for imaging the product by the OCT. Due to an increased reflectance of the product due to the presence of the nano-particles, the product may be imaged better using the OCT compared to conventional products. In particular, the product can be distinguished better from materials of a body (especially a mammal or human body) having a same or similar extinction and reflectance.

According to an embodiment, a system is provided comprising an OCT-system having a light source for emitting an OCT measurement light beam along an OCT measurement light path to an object, a detector for detecting OCT measurement light returning from the object and a product of the previously described kind. The product is disposable in the OCT measurement light path in the vitreous humor or generally in the interior of an eye of a patient (in particular in the anterior chamber and/or the posterior chamber). The light source may emit light having wavelengths in the visible light wavelength region and/or near-infrared light wavelength region, wherein a spectral width of the light source is configured in a way that a coherence length of the light emitted by the light source is between a few micrometers and a few tens of micrometers. A portion of the OCT measurement light beam emitted by the light source is guided to an object along an OCT light path which may comprise mirrors, lenses and/or fiber optics, wherein the light penetrates the object up to a particular penetration depth depending on the wavelength and the materials within the object. A portion of the penetrating measurement light is reflected depending on a reflectance within the object and is superimposed interferometrically with a second portion of the light emitted by the light source which is reflected at a reference area. The superimposed light is detected by a detector and converted into electric signals representing the intensity of the detected superimposed light. Due to the comparatively short coherence length of the OCT measurement light, constructive interference may only be observed if the optical path traversed by the OCT measurement light to and from the object differs by less than the coherence length of the OCT measurement light from the optical path traversed by the second portion of the light reflected from the reference area.

Different embodiments provide different configurations of an OCT-system. The different configurations of an OCT-system differ in the way a scanning of structural information along the direction of depth (axial direction) is performed as well as in the way the superimposed light is detected.

According to Time-Domain-OCT (TD-OCT), the reference area at which the second portion of the light emitted by the light source is reflected is displaced in order to obtain structural information of the object from different depths. An intensity of the superimposed light can, in this case, be detected by a photo detector.

In Frequency-Domain-OCT (FD-OCT), the second portion of the OCT measurement light emitted by the light source is also reflected by a reference area, however, the reference area does not need to be displaced in order to obtain structural information from different depths inside the object. Instead, the superimposed light is separated into spectral sections by a spectrometer and the spectral sections are detected by, for example, a spatially-resolving detector such as a CCD camera. By Fourier transforming the obtained spectrum of the superimposed light, structural information of the object along the direction of depth may be obtained (Fourier-Domain-OCT).

Another configuration of FD-OCT is Swept-Source-OCT (SS-OCT). A spectrum of superimposed light is recorded after another in time, wherein a central wavelength of a very narrow band illumination light is continuously changed and, simultaneously, the superimposed light is detected using a photo diode.

The product comprising nano-particles in at least one portion of the product is disposable in the OCT measurement light path and, therefore, may be imaged.

According to an embodiment, the system further includes a calculation system configured to determine a lateral density distribution of data representing the object based on the OCT measurement light detected by the detector. This may, for example, be performed in dependence of an optical path being traversed in the traversed product. An optical path through the traversed product corresponds to a product of a path D traversed through the product and the refractive index n of the product in the traversed region. The refractive index n of the product may be greater than 1. At small concentrations of the nano-particles, the refractive index of the product may be approximated to a first order as the refractive index of the supporting agent. In general, the refractive index depends the wavelength of the OCT measurement light. The refractive index of vacuum is exactly 1 for every wavelength used. For solids, gels or liquids, the refractive index in the region of visible or near-infrared light is between 1.2 and 2.0. Therefore, the optical path of the OCT measurement light through the traversed product is greater than the geometric path through the traversed product. In order to correct for thus generated artifacts of the structural information of regions disposed downstream of the traversed product, the spatial position of the structures imaged by the OCT-system and being disposed downstream of the illuminated product are displaced by twice a difference of the optical path through the traversed product and the geometric path through the traversed product by a processing system in order to obtain corrected structural information of the object.

According to an embodiment, a method is provided comprising illuminating an object using an OCT measurement light beam along an OCT measurement light path, disposing one of the above described products in the OCT measurement light path, detecting OCT measurement light returning from the object and the product, and determining a lateral density distribution of data representing the object based on the detected OCT measurement light.

According to an embodiment, a method of producing one of the above described products is provided, wherein the method comprises providing a viscoelastic substrate or a silicone oil or a perfluorocarbon as a supporting agent and mixing the supporting agent with nano-particles. The mixing of the supporting agent with the nano-particle may be performed, for example, by interfusing. The nano-particles may be distributed homogeneously or inhomogeneous in the supporting agent.

Note that, in this context, the terms for enumerations used throughout this description and the claims "comprise", "contain", "have" and "with" as well as their respective grammatical derivations are to be regarded as open, i.e. not closed, enumeration of features such as method steps, units, regions, sizes and the like, and shall not in any sense exclude a presence of other or additional features or groups of other or additional features.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

Figure 1A:
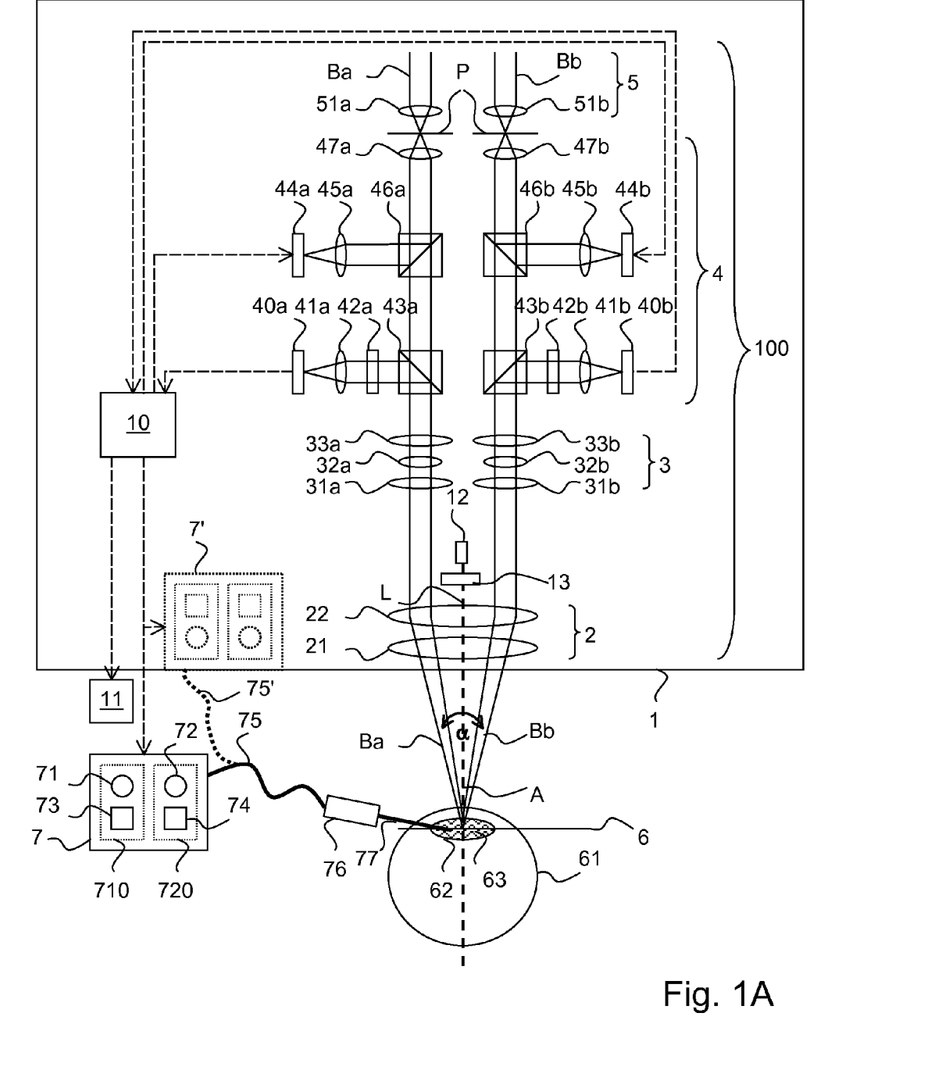
FIG. 1A schematically shows a configuration of an ophthalmology microscopy-system according to a first embodiment.
Figure 1B:
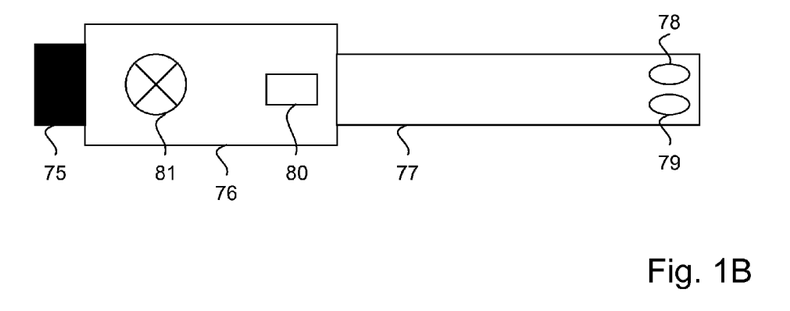
FIG. 1B schematically shows a magnified configuration of a hand piece coupled to the ophthalmology microscopy-system of FIG. 1A.

With reference to FIGS. 1A and 1B, a first embodiment is described in the following.

The ophthalmology microscopy-system includes a housing 1 housing an imaging system 100 comprising an objective system 2, a zoom system 3, a tube system 4 and an ocular system 5. The imaging system 100 provides two imaging beam paths Ba, Bb guided side by side in the objective system 2, the zoom system 3, the tube system 4 and the ocular system 5. In front of the objective system 2, an ophthalmology loupe (not shown) may be disposable along both imaging beam paths Ba, Bb.

The imaging beam paths Ba, Bb intersect in a focal plane 6 of the objective system 2 enclosing a stereo angle α. This stereo angle is measured between central rays of the imaging beam paths Ba, Bb (not shown in FIG. 1). Depending on a chosen working distance of the objective system 2, the stereo angle α amounts to values between 0.5° and 10°. Each of these stereoscopic imaging beam paths Ba, Bb image the focal plane 6 of the objective system 2 and an object disposable in the object plane 6, e.g. an eye 61, into a two-dimensional intermediate image P in a magnifying way so that, when observing both imaging beam paths Ba, Bb, a magnified three-dimensional image perception can be obtained.

In the embodiment shown, the objective system 2 is configured having two elements and includes two optical lenses 21, 22 being traversed one after another by the stereoscopic imaging beam paths Ba, Bb. The stereoscopic imaging beam paths Ba, Bb are guided in common optical lenses 21, 22. The distance between the optical lenses 21, 22 is variable along their common optical axis A in order vary a position of the focal plane 6 of the objective system 2. In the embodiment shown, the working distance of the objective system 2 may amount to a value between 150 mm and 200 mm. The working distance is the distance of the focal plane 6 to the front lens vertex of the optical lens 21 of the objective system 2 along the stereoscopic imaging beam paths Ba, Bb. The optical lenses 21, 22 of the objective system 2 image the focal plane 6 to infinity so that an afocal interface is disposed between the objective system 2 and the zoom system 3. It is emphasized that the present disclosure is not limited to objective systems having two elements or afocal objective systems. In general, objective systems of multiple elements and also non-afocal objective systems may be used.

In the embodiment shown, the zoom system 3 is configured having three elements and includes three pairs of optical lenses 31a, 31b, 32a, 32b, 33a, 33b being traversed one after another by only one of the two stereoscopic imaging beam paths Ba, Bb. Therefore, the stereoscopic imaging beam paths Ba, Bb are guided in separate optical lenses 31a, 32a, 33a or 31b, 32b, 33b in the zoom system 3, respectively. The distance between the optical lenses 31a, 32a, 33a and 31b, 32b, 33b, respectively, is variable along their optical axes (not shown) in order to vary an image magnification generated by the zoom system 3. It is emphasized that the present disclosure is not limited to a zoom system having three elements. In general, a zoom system having multiple elements may be used. Also, the zoom system 3 images both the stereoscopic imaging beam paths Ba, Bb into infinity so that an afocal interface is disposed between the zoom system 3 and the tube system 4.

The tube system 4 comprises, along each of both stereoscopic imaging beam paths Ba, Bb, a first beam splitter 43a, 43b and a second beam splitter 46a, 46b as well as tube lenses 47a, 47b, wherein each of these components is traversed one after another by the two stereoscopic imaging beam paths Ba, Bb. The first beam splitters 43a, 43b are oriented in a way that a portion of the radiation guided in each of the imaging beam paths Ba, Bb is coupled out. The second beam splitters 46a, 46b are oriented in a way that additional radiation is superimposed onto radiation guided in each of the imaging beam paths Ba, Bb. The first and second beam splitters 43a, 46a and 43b, 46b, respectively, and the tube lenses 47a, 47b each are traversed by only a single one of the two stereoscopic imaging beam paths Ba, Bb.

The first beam splitters 43a, 43b guide a portion of the radiation guided in each of the imaging beam paths Ba, Bb to a photo detector such as a color camera 40a, 40b via an observation filter 42a, 42b and camera optic 41a, 41b. The color cameras 40a, 40b output electric signals comprising image data wherein the image data represents the image of an object such as the anterior chamber 62 of the eye 61, wherein the image is generated by the objective system 2, the zoom system 3 and the camera optic 41a, 41b. The color cameras 41a, 41b are, in this case, configured as releasable elements.

The second beam splitters 46a, 46b superimpose an image visualized on an LCD-display 44a, 44b onto each of the radiation guided in the imaging beam paths Ba, Bb, respectively. An appropriate optic 45a, 45b is provided between the LCD-display 44a, 44b and the respective second beam splitter 46a, 46b.

Each of the tube lenses 47a, 47b images one beam path of the stereoscopic imaging beam paths Ba, Bb into an intermediate image P.

The intermediate images P may be observed by a user via optical lenses 51a, 51b of the ocular system 5. The present disclosure is not limited to ocular systems having only a single optical lens per imaging beam path. Instead, ocular systems may include multiple optical lenses per imaging beam path which are traversed one after another.

It is emphasized that the optical lenses of the imaging system 100 may be simple lens elements or cemented elements, wherein the cemented elements consist of at least two optical lenses of materials having different refractive indices and are formed by gluing.

The housing 1 of the ophthalmology microscopy-system further houses an illumination system having a source of radiation being a xenon lamp 12. The illumination system provides an illumination beam path L coinciding, in the embodiment shown, with the optical axis A of the optical lenses 21 and 22 of the objective system 2 and traversing the optical lenses 21 and 22 of the objective system 2. A switchable illumination filter 13 is disposed in front of the xenon lamp 12. The radiation emitted by the xenon lamp 12 has a spectral width of roughly 400 nm in the visible light wavelength region. It is emphasized that the illumination filter is only necessary if the source of radiation emits a broad band radiation as in the present case. Alternative to a combination of broad band source of radiation and a switchable illumination filter, also one or multiple narrow band sources of radiation such as a laser or a light emitting diode (LED) may be used. In this respect, a narrow band source of radiation refers to a source of radiation emitting at least 90% of the emitted power of radiation within a spectral width of less than 50 nm.

The housing 1 of the ophthalmology microscopy-system further houses a controller 10 connected to the color cameras 40a, 40b and the LCD-displays 44a, 44b as well as an external 3D-monitor 11 and a rinsing-suction-apparatus 7 by control wires indicated as dashed lines in FIG. 1A.

The rinsing-suction-apparatus 7 includes a housing containing a suction apparatus 710 having a suction pump 71 connected to a reservoir 73 via a pressure-resistant conduct (not shown) and a rinsing apparatus 720 having a rinsing pump 72 connected to a reservoir of liquid 74 via a pressure-resistant conduct (not shown). Furthermore, the rinsing-suction-apparatus 7 includes a hand piece 76 as well as a suction head 77 mounted to the hand piece 76. The hand piece 76 comprising the suction head 77 is connected to the suction pump 71 and the rinsing pump 72 via a pressure-resistant conduct 75. In the embodiment shown, the pressure-resistant conduct 75 also comprises control wires for supplying the hand piece with electric current and control signals from the controller 10.

As shown in FIG. 1B, the hand piece 76 of the rinsing-suction-apparatus 7 includes an indicator, in this case, a light emitting diode 81. Furthermore, the suction head 77 comprises two openings 78, 79, each of which is in fluidic connection to the suction pump 71 and the rinsing pump 72, respectively. Furthermore, a sound generator 80 is disposed in the hand piece 76, wherein the sound generator 80 is mechanically coupled to the suction head 77.

In the following, a principle of operation of the previously described ophthalmology microscopy-system is described in the context of a cataract-surgery. Here, only a temporal section of the cataract-surgery is described and a description of other temporal sections (such as anesthesia and wound treatment) is omitted.

First, the controller 10 of the ophthalmology microscopy-system outputs control signals causing the eye 61 of a patient being illuminated with white light using the xenon lamp 12; thus, the illumination filter 13 is not disposed in the illumination beam path L. Further, the controller 10 controls the objective lenses 21, 22 so that an eye chamber 62 of the eye 61 of the patient is disposed in the focal plane 6 of the objective system 2. In turn, the eye chamber 62 is imaged via the objective system 2, the zoom system 3, the tube system 4, the oculars 5 and the color cameras 40a, 40b, respectively, in a magnifying way. The observation filters 42a, 42b are not disposed in front of the color cameras 40a, 40b. The image data generated by the color cameras 40a, 40b are output as electric signals to the controller 10 and visualized on the 3D-monitor 11 by the controller.

Then, the cornea of the eye 61 is cut open using a scalpel and the suction head 77 of the rinsing-suction-apparatus 7 is introduced into the eye chamber 62.

The controller 10 activates the sound generator 80 disposed in the hand piece 76 due to a user-input via a not shown user-interface (such as a pedal), wherein the sound generator 80 outputs supersonic sound into the interior of the eye chamber 62 via the suction head 76. The supersonic sound shatters a (not shown) lens of the eye 61 of the patient. In order to remove the shattered pieces of the lens from the eye 61, the controller 10 now activates the rinsing pump 62 of the rinsing-suction-apparatus 7. The rinsing pump 72 rinses a supporting agent, in the present embodiment, a viscoelastic substrate 63 containing 0.05% fluorescein, into the eye chamber 62 via the opening 79 in the suction head 77, wherein the viscoelastic substrate 63 resides in the reservoir of liquid 74.

Then, the controller 10 controls the illumination filter 13 so that it is disposed in the illumination beam path L. The illumination filter 13 has a transmittance greater than 90% for radiation of wavelengths of the excitation band of fluorescein and a transmittance of less than 3% for radiation of wavelengths of the fluorescent band of fluorescein. Furthermore, the controller 10 controls the observation filters 42a, 42b so that they are disposed in front of the color cameras 40a, 40b. The observation filters 42a, 42b have a transmittance of less than 2% for radiation of wavelengths of the excitation band of fluorescein and a transmittance greater than 95% for radiation of wavelengths of the fluorescent band of the fluorescein. Due to this setting of the illumination filter 13 and the observation filters 42a, 42b, an intensity of radiation detected by the color cameras 40a and 40b essentially corresponds to fluorescent radiation of the viscoelastic substrate 63 comprising fluorescein. The controller 10 compares the electric signals output by the color cameras 40a, 40b with a threshold-value predetermined by a user in order to determine whether the intensity of the fluorescent radiation detected by the color cameras 40a, 40b is greater than or equal to the threshold-value. This way, it can be determined whether and how much viscoelastic substrate 63 comprising fluorescein has been pumped into the eye chamber 62.

As soon as the threshold-value is exceeded, the controller 10 deactivates the rinsing pump 72 and activates the suction pump 71 sucking off the viscoelastic substrate 63 comprising fluorescein together with the shattered pieces of the lens into the reservoir 73 via the opening 78 in the suction head 77. The controller 10 increases the used suction rate of the suction pump 71 if the intensity of the fluorescent radiation detected by the color cameras 40a, 40b increases. As soon as the threshold-value is no longer exceeded, the controller 10 deactivates the suction pump 71. This prevents that too much liquid is sucked off the eye 61 of the patient. In order to indicate the activating of the suction pump 71 and the suction rate selected by the controller 10 to a user, the controller 10 controls the light emitting diode 81 so that different colors are emitted in dependence of the suction rate.

According to an embodiment, the controller 10 determines, by digital image processing of the images output by the color cameras 40a, 40b, a distance of the free end of the suction head 77 to the viscoelastic substrate 63 comprising fluorescein and considers this distance when selecting the suction rate of the suction pump 71. For example, the suction rate may be reduced or the suction pump 71 may be switched off if the distance between the free end of the suction head 77 and the viscoelastic substrate 63 comprising fluorescein exceeds a threshold-value.

Finally, the controller 10 superimposes information about the amount of viscoelastic substrate 63 comprising fluorescein being sucked off by the suction pump 71 via the LCD-displays 44a, 44b onto the observation beam paths Ba, Bb.

Although a stereo microscopy system having one pair of stereoscopic imaging beam paths Ba, Bb has been described hereinbefore, the present disclosure is not limited thereon. Alternatively, multiple pairs of stereoscopic beam paths may be provided. Furthermore alternative, it may also so be a monoscopic system having only a single imaging beam path.

Figure 2A:
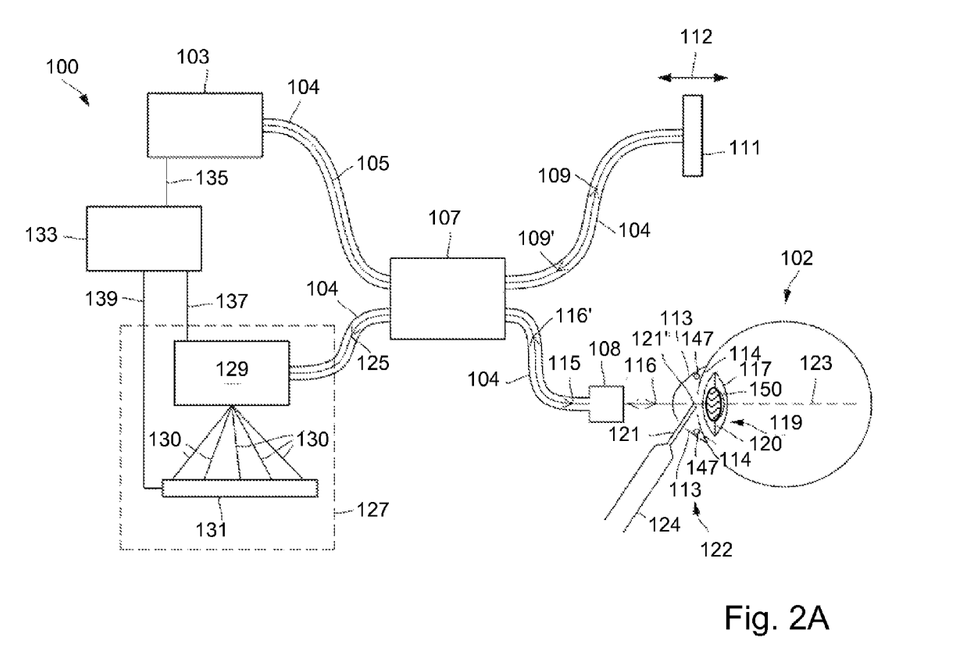
FIG. 2A schematically shows a configuration of an OCT-system according to a second embodiment.
Figure 2B:
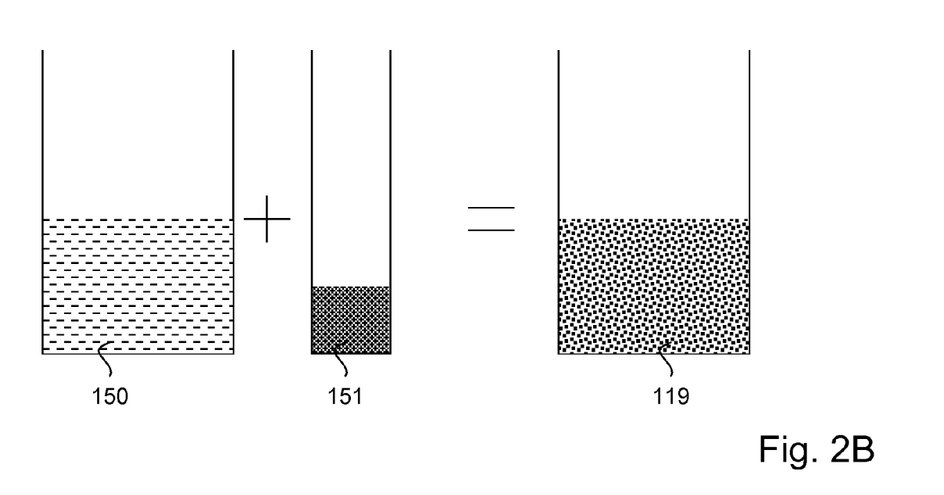
FIG. 2B schematically shows a product to be used in the OCT-system of FIG. 2A.

With reference to FIGS. 2A and 2B, a second embodiment is described in the following.

FIG. 2A schematically illustrates a simplified configuration of an OCT-system 100 used for inspection of a human eye 102. In particular, the OCT-system 100 may be advantageously used during a surgery of an eye, in particular a cataract-surgery. The embodiment of an OCT-system illustrated schematically in FIG. 2A is a Fourier domain OCT-system (FD-OCT-system) commonly referred to as spectral domain OCT-system. Other embodiments include a swept-source-OCT-system (SS-OCT-system) or a time domain OCT-system (TD-OCT-system).

The OCT-system 100 includes a light source 103 generating OCT measurement light 105 according a particular spectrum. The light source 103 includes a superluminescent diode configured to generate OCT measurement light 105 having a spectrum having a central wavelength and a spectral width. The central wavelength amounts to roughly 1000 nm and has a spectral width of 20 nm to 30 nm. Instead of using a superluminescent diode, the light source 103 may alternatively include a white light source and, in addition, a spectral filter disposed in an OCT measurement beam path in order to approximately provide the above described spectrum. The OCT measurement light 105 generated by the light source 103 is guided to a fiber optical splitter/coupler 107 via an optical fiber 104. The fiber optical splitter/coupler 107 is configured to split the OCT measurement light 105 into two portions of light 109 and 115. The portion of light 109 is guided to a reflecting reference area 111 via an optical fiber in order to form the light portion 109'. The reference area 111 is displaceable in a direction indicated by a double arrow 112 in order to be able to vary a path length traversed by the portions of light 109 and 109'.

The other portion of light 115 separated from the OCT measurement light 105 is guided via an optical fiber 104 to a scanner 108 having an illumination optic. The scanner 108 having the illumination optic is configured to form a focused OCT measurement light beam 116 having a defined cross-sectional extension in a region of inspection, wherein the defined cross-sectional extension amounts to roughly 10 μm to 50 μm. The scanner 108 having the illumination optic may also be configured to form a measurement light beam 116 consisting of parallel light beams, in particular, if a back region of the eye such as the retina is to be inspected.

The scanner 108 having the illumination optic is further configured to guide the OCT measurement light bundle 116 laterally over a field of inspection of the human eye 102. For this, the scanner 108 may include one or multiple mirrors pivotable about different axes.

The OCT measurement light bundle 116 interacts with structures of the human eye 102 such as the cornea 113, the iris 114, the capsular bag 119, a supporting agent 119 comprising nano-particles as well as a suction head 121, the suction opening 121' of which is disposed in proximity of the capsular bag 117. The interaction of the OCT measurement light bundle 116 includes different physical processes such as scattering, reflection and absorption. A fraction of the radiated OCT measurement light bundle 116 is reflected in an essentially counter-directed direction, collected by the scanner 108 and guided back into the optical fiber 104 as a light 116'.

The light 116' carries structural information about the region of inspection of the eye into which the OCT measurement light bundle 116 has penetrated. Light 116' is guided to the fiber optical splitter/coupler 107 where it is superimposed with the portion of light 109' reflected at the reference area 111 in order to form superimposed light 125. The superimposed light 125 is guided to a spectrometer 127 via the optical fiber 104. The spectrometer 127 includes a dispersion apparatus 129 in order to disperse the superimposed light 125 spectrally into spatially separated portions of light 130. Each portion of light 130 includes light waves having wavelengths of a distinct wavelength region. In particular, the wavelength regions of different portions of light 130 are different. The spatially separated portions of light 130 are detected by the spatially resolving detector 131 providing a plurality of pixels in order to separately determine intensities of the different spatially separated portions of light 130 and generate electric signals thereof.

The electric signals are transmitted to a control- and processing system 133 via a signal wire 139, wherein the control- and processing system 133 is configured to process the electric signals and to determine data representing a structure of the region of inspection of the eye based thereon. The intensities of the detected spectral portions of light 130 represent a spectrum of the superimposed light 125 from which, after subtraction of a background, spectral resembling and determining of the Fourier transform, structural information along a direction of depth 123 may be determined. The control- and processing system 133 may also be configured to control characteristics of the light source 103 with respect to its spectrum via a signal wire 135 and may further be configured to vary a dispersion strength of the dispersion apparatus 129 via a signal wire 137. Based on the data representing the structure of the region of inspection of the eye 102, an image of the region of inspection of the eye may be determined and, for example, be displayed on a monitor (not shown). The display may include, for example, a representation of a volume or a sectional view.

Some embodiments provide products which can be used advantageously during an inspection or a surgery using the OCT-system 100. The products provide, on the one hand, an appropriate reflectance in order to be imaged by the OCT-system 100, however, on the other hand, said products attenuate the OCT measurement light bundle 116 merely insofar as anatomic structures of the eye 102 disposed downstream are still detectable by the OCT-system 100 and, therefore, may still be imaged.

In the embodiment shown, a supporting agent 119 of silicone oil is introduced into a capsular bag 117 of the eye, wherein the silicone oil comprises nano-particles providing an increase of the signal of the supporting agent 119 detectable by the OCT-system 100 compared to a supporting agent without nano-particles.

A suction head 121 of a suction apparatus 122 is introduced into the capsular bag 117, wherein the suction apparatus 122 is provided to suck off a shattered natural lens from the capsular bag 117 during a cataract-surgery. The suction apparatus 122 may be configured as a phako hand piece allowing for phakoemulsification during which lens fragments may be sucked off using the phako hand piece.

A surgeon introduces the suction apparatus 122, and in particular the suction opening 121' of the suction head 121, to the region of surgery using a phako hand piece 124 while being inspected by the OCT-system 100 in order to approach the suction opening 121' to an incision at the capsular bag 117 as close as possible in order to suck off a previously shattered natural lens. The increased contrast of the imaged supporting agent 119 comprising nano-particles simplifies an exact positioning of the suction opening 121' of the suction head 121 in the region of the supporting agent 119 for the surgeon and, therefore, a full removal of the supporting agent 119 from the eye 102.

During an inspection of the eye 102, the supporting agent 119 comprising nano-particles is disposed in a beam path of the measurement light bundle 116 of the OCT-system 100. An intensity of the OCT measurement light bundle 116 incident onto the supporting agent 119 comprising nano-particles is referred to as $I_e$, an intensity of the OCT measurement light bundle transmitted through the supporting agent 119 having nano-particles is referred to as $I_t$. Due to the presence of the nano-particles in the supporting agent 119, the intensity $I_t$ of the transmitted OCT measurement light is less than the intensity $I_e$ of the incident OCT measurement light. The extinction previously defined in Equation (2) may amount to a value of up to 10. Regardless of this strong attenuation of the intensity of the OCT measurement light bundle 116 having transmitted through the supporting agent 119 comprising nano-particles, an anatomic structure of the eye 102 disposed downstream of the supporting agent 119 comprising nano-particles, in this case the capsular bag 117, may be detected using the OCT-system 100 due to its high sensitivity.

The sensitivity of an OCT-system is commonly defined as the minimum reflectance of the sample-arm of the interferometer at which the signal-to-noise ratio becomes 1. Instead of determining the minimum reflectance of the sample-arm, the maximum attenuation or extinction of the OCT measurement light bundle may be determined at which an ideal mirror may just still be detectable by OCT measurement light having the intensity $I_t$. Therefore, the sensitivity in decibel is given by $$\text{sensitivity} = -10 \cdot \log_{10}\left(\frac{I_t}{I_e}\right) \quad \text{Equation (4)}$$

Sensitivities of modern OCT-systems were analyzed in the publication "Performance of fourier domains vs. time domains optical coherence tomography", R. Leitgeb et al., Optics Express, Vol. 11, No. 8, pages 889 to 894. A sensitivity up to 108 dB may be achieved. Due to the path traversed twice through the product, based on Equations (2) and (4), the maximum extinction of a product, if structures disposed downstream are just yet to be detected is given by:

$$\text{max} \cdot \text{extinction} = \frac{1}{2} \cdot \frac{1}{10} \cdot \text{sensitivity} \quad \text{Equation (5)}$$

Therefore, if the extinction of the supporting agent 119 comprising nano-particles along the transmission direction given by the direction of the incident OCT measurement light bundle 116 is less than the maximum extinction defined by Equation (5), hence, in particular less than 5, a boundary surface defined by the capsular bag 117 should still be detectable by the imaging OCT-system 100.

The refractive index n of the supporting agent 119 comprising nano-particles essentially corresponds to the refractive index $n_M$ of the surrounding medium (in this case, aqueous liquid within the eye)

FIG. 2B schematically shows producing a supporting agent 119 comprising nano-particles.

A supporting agent 150 without nano-particles (in this case, perfluorocarbon) is stirred with nano-particles 151 (in this case, gold beads having a diameter of 100 nm) so that an emulsion is formed. The amount of nano-particles 151 is chosen so that the nano-particles 151 provide an increased extinction per traversed centimeter of less than 6 and a reflectance of the product is increased in the visible light wavelength region due to the presence of the nano-particles 151 by at least 10%.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An ophthalmology microscopy-system for application in a cataract-surgery, wherein the ophthalmology microscopy-system is an optical reflected light microscope and includes:
   an imaging system providing two imaging beam paths imaging an object disposable in a focal plane of the imaging system in a magnifying way to a multidimensional image of the object, wherein the imaging beam paths intersect in the focal plane enclosing an angle between 0.5° and 10° ;
   at least one photo detector configured to detect an intensity of radiation guided in at least one of the two imaging beam paths of the imaging system and to output an electric signal depending on the detected intensity of the radiation;
   a suction apparatus having a suction pump connectable to a suction head, wherein the suction head is introducible into an eye of a patient; and
   a controller configured to control a suction rate of the suction pump of the suction apparatus depending on the electric signal output by the at least one photo detector,
   wherein the at least one photo detector is configured to detect an intensity of a radiation emitted by a substitute material disposed in the eye of the patient and to output the electric signal depending on the detected intensity of the radiation emitted by the substitute material disposed in the eye of the patient.

2. The ophthalmology microscopy-system according to claim 1, wherein the substitute material is a material selected from a group of materials comprising a viscoelastic substrate, a silicone oil and a perfluorocarbon.

3. The ophthalmology microscopy-system according to claim 2, wherein the viscoelastic substrate contains at least 0.1 wt % of at least one of chondroitin sulfate, sodium hyaluronate, hydroxypropylmethylcellulose, and a sodium salt of hyaluronic acid.

4. The ophthalmology microscopy-system according to claim 1, wherein the controller is configured to control the suction pump of the suction apparatus in a way that the suction rate of the suction pump increases when the intensity of the radiation emitted by the substitute material disposed in the eye of the patient and detected by the at least one photo detector increases.

5. The ophthalmology microscopy-system according to claim 1, wherein the controller is configured to deactivate the suction pump of the suction apparatus as soon as the intensity of the radiation emitted by the substitute material disposed in the eye of the patient and detected by the at least one photo detector is less than a predetermined threshold-value.

6. The ophthalmology microscopy-system according to claim 1, wherein the controller is configured to activate the suction pump of the suction apparatus as soon as the intensity of the radiation emitted by the substitute material disposed in the eye of the patient and detected by the at least one photo detector reaches or exceeds a threshold-value.

7. The ophthalmology microscopy-system according to claim 1, wherein the substitute material contains a fluorescent dye.

8. The ophthalmology microscopy-system according to claim 1, wherein the suction head includes an indicator, the status of which changes depending on the electric signal output by the at least one photo detector.

9. An ophthalmology microscopy-system for application in a cataract-surgery, wherein the ophthalmology microscopy-system includes:
  an imaging system providing at least one imaging beam path imaging an object disposable in a focal plane of the imaging system in a magnifying way to a multidimensional image of the object;
  at least one photo detector configured to detect an intensity of radiation guided in at least one of the at least one imaging beam path and to output an electric signal depending on the detected intensity of the radiation;
  a suction apparatus having a suction pump connectable to a suction head, wherein the suction head is introducible into an eye of a patient; and
  a controller configured to control a suction rate of the suction pump of the suction apparatus depending on the electric signal output by the at least one photo detector,
  wherein the at least one photo detector is configured to detect an intensity of a radiation emitted by a substitute material disposed in the eye of the patient and to output the electric signal depending on the detected intensity of the radiation emitted by the substitute material disposed in the eye of the patient
  wherein the substitute material contains a fluorescent dye,
  wherein the ophthalmology microscopy-system further includes an illumination system providing an illumination beam path and having at least one mode of operation in which radiation guided in the illumination beam path contains, in at least a section of the illumination beam path, an excitation band of the fluorescent dye and, simultaneously, is essentially free of a fluorescent band of the fluorescent dye; and
  wherein the at least one photo detector is configured to suppress detecting radiation of the excitation band of the fluorescent dye relative to detecting radiation of the fluorescent band of the fluorescent dye.

10. An ophthalmology microscopy-system for application in a cataract-surgery, wherein the ophthalmology microscopy-system includes:
  an imaging system providing at least one imaging beam path imaging an object disposable in a focal plane of the imaging system in a magnifying way to a multidimensional image of the object;
  at least one photo detector configured to detect an intensity of radiation guided in at least one of the at least one imaging beam path and to output an electric signal depending on the detected intensity of the radiation;
  a suction apparatus having a suction pump connectable to a suction head, wherein the suction head is introducible into an eye of a patient; and
  a controller configured to control a suction rate of the suction pump of the suction apparatus depending on the electric signal output by the at least one photo detector,
  wherein the at least one photo detector is configured to detect an intensity of a radiation emitted by a substitute material disposed in the eye of the patient and to output the electric signal depending on the detected intensity of the radiation emitted by the substitute material disposed in the eye of the patient
  wherein the substitute material contains a fluorescent dye,
  wherein the imaging system includes at least one optical observation filter suppressing a transmittance of radiation of an excitation band of the fluorescent dye relative to a transmittance of radiation of the fluorescent band of the fluorescent dye, wherein the at least one optical observation filter is disposed in the at least one imaging beam path in front of the at least one photo detector in a mode of operation;
  wherein the ophthalmology microscopy-system further includes an illumination system providing an illumination beam path and having at least one mode of operation in which radiation guided in the illumination beam path contains, in at least a section of the illumination beam path, the excitation band of the fluorescent dye and, simultaneously, is essentially free of a fluorescent band of the fluorescent dye; and
  wherein the at least one photo detector is configured to detect radiation of the excitation band of the fluorescent dye.

11. An ophthalmology microscopy-system for application in a cataract-surgery, wherein the ophthalmology microscopy-system includes:
  an imaging system providing at least one imaging beam path imaging an object disposable in a focal plane of the imaging system in a magnifying way to a multidimensional image of the object;
  at least one photo detector configured to detect an intensity of radiation guided in at least one of the at least one imaging beam path and to output an electric signal depending on the detected intensity of the radiation;
  a suction apparatus having a suction pump connectable to a suction head, wherein the suction head is introducible into an eye of a patient; and
  a controller configured to control a suction rate of the suction pump of the suction apparatus depending on the electric signal output by the at least one photo detector, the system, further comprising:
  a rinsing apparatus having a reservoir of liquid and a rinsing pump, wherein the rinsing pump is connected to the reservoir of liquid via pressure-resident conducts and is connectable to the suction head, wherein the rinsing pump is configured to pump liquid from the reservoir of liquid to the suction head and output the liquid into the eye of the patient via an opening in the suction head; and
  wherein the controller is configured to control a delivery rate of the rinsing pump of the rinsing apparatus depending on the electric signal output by the at least one photo detector.

12. A method of operating an ophthalmology microscopy-system during a cataract-surgery, wherein the ophthalmology microscopy-system comprises an optical reflected light microscope and a suction apparatus connectable to a suction head introducible into an eye of a patient, wherein the optical reflected light microscope includes an imaging system providing two imaging beam paths imaging an object disposable in a focal plane of the imaging system in a magnifying way to a multidimensional image of the object, wherein the imaging beam paths intersect in the focal plane enclosing an angle between 0.5° and 10°, wherein the method comprises:
- detecting radiation emitted by one of a viscoelastic substrate, a silicone oil and perfluorocarbon disposed in the eye of the patient; and
- automatically adjusting a suction rate of the suction pump of a suction apparatus, wherein the automatic adjusting of the suction rate depends on an intensity of the detected radiation.

* * * * *